(12) United States Patent
Lautenschlaeger

(10) Patent No.: US 11,837,362 B2
(45) Date of Patent: Dec. 5, 2023

(54) METHOD FOR PROVIDING AT LEAST ONE IMAGE DATASET, STORAGE MEDIUM, COMPUTER PROGRAM PRODUCT, DATA SERVER, IMAGING DE-VICE AND TELEMEDICINE SYSTEM

(71) Applicant: Siemens Healthcare GmbH, Erlangen (DE)

(72) Inventor: Stefan Lautenschlaeger, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/027,858

(22) Filed: Sep. 22, 2020

(65) Prior Publication Data

US 2021/0098125 A1    Apr. 1, 2021

(30) Foreign Application Priority Data

Sep. 26, 2019   (EP) .................................... 19199917

(51) Int. Cl.
| | |
|---|---|
| *G16H 40/67* | (2018.01) |
| *G16H 10/60* | (2018.01) |
| *G16H 30/40* | (2018.01) |
| *H04L 67/04* | (2022.01) |
| *H04N 1/00* | (2006.01) |
| *H04N 7/18* | (2006.01) |
| *H04N 23/80* | (2023.01) |

(52) U.S. Cl.
CPC ............. *G16H 40/67* (2018.01); *G16H 10/60* (2018.01); *G16H 30/40* (2018.01); *H04L 67/04* (2013.01); *H04N 1/00244* (2013.01); *H04N 7/185* (2013.01); *H04N 23/80* (2023.01)

(58) Field of Classification Search
CPC ........ G16H 10/60; G16H 30/20; G16H 30/40; G16H 40/67; H04L 67/04; H04N 1/00244; H04N 5/23229; H04N 7/185
See application file for complete search history.

(56) References Cited

U.S. PATENT DOCUMENTS

| | | | | |
|---|---|---|---|---|
| 6,481,887 B1 * | 11/2002 | Mirabella | ............ | A61B 6/4405 296/24.38 |
| 11,145,395 B1 * | 10/2021 | Mitchell | ................ | G16H 30/40 |

(Continued)

FOREIGN PATENT DOCUMENTS

| | | |
|---|---|---|
| CN | 102231172 A | 11/2011 |
| CN | 106777905 A | 5/2017 |
| EP | 3506277 A1 | 7/2019 |

*Primary Examiner* — Peter D Le
(74) *Attorney, Agent, or Firm* — Harness, Dickey & Pierce, P.L.C.

(57) ABSTRACT

A storage medium, computer program product, data server, imaging device, telemedicine system and method are for providing at least one image dataset. In an embodiment, the method includes processing at least one raw image dataset, acquired from a patient by an imaging device of a mobile unit, to create a processed image dataset; generating a reduced image dataset by reducing an amount of data of the processed image dataset; and storing at least one of the at least one raw image dataset, the processed image dataset and the reduced image dataset on a data server, the data server being part of the mobile unit and being connected to a network.

17 Claims, 5 Drawing Sheets

(56) References Cited

U.S. PATENT DOCUMENTS

| | | | | |
|---|---|---|---|---|
| 2001/0037191 | A1* | 11/2001 | Furuta | G06T 7/596 |
| | | | | 703/6 |
| 2002/0016718 | A1* | 2/2002 | Rothschild | H04N 1/32128 |
| | | | | 705/2 |
| 2003/0050062 | A1* | 3/2003 | Chen | H04L 65/103 |
| | | | | 455/435.1 |
| 2003/0060808 | A1* | 3/2003 | Wilk | A61B 34/37 |
| | | | | 606/1 |
| 2007/0294105 | A1* | 12/2007 | Pierce | G16H 20/13 |
| | | | | 600/300 |
| 2008/0021730 | A1* | 1/2008 | Holla | G16H 40/67 |
| | | | | 705/2 |
| 2008/0021834 | A1 | 1/2008 | Holla et al. | |
| 2010/0114588 | A1* | 5/2010 | Moitra | G16H 10/60 |
| | | | | 705/2 |
| 2010/0279678 | A1* | 11/2010 | Li | H04L 67/2828 |
| | | | | 455/422.1 |
| 2011/0072425 | A1* | 3/2011 | Lemonnier | G06Q 20/322 |
| | | | | 717/178 |
| 2012/0324397 | A1 | 12/2012 | Patz et al. | |
| 2013/0130218 | A1* | 5/2013 | Hargreaves | G16H 50/30 |
| | | | | 434/362 |
| 2014/0006055 | A1* | 1/2014 | Seraly | G06Q 10/10 |
| | | | | 705/3 |
| 2014/0344896 | A1* | 11/2014 | Pak | G06F 21/74 |
| | | | | 726/4 |
| 2015/0006669 | A1* | 1/2015 | Kauffmann | H04L 67/10 |
| | | | | 709/217 |
| 2015/0086133 | A1* | 3/2015 | Grady | G16H 30/20 |
| | | | | 382/278 |
| 2015/0088547 | A1* | 3/2015 | Balram | G16H 40/67 |
| | | | | 705/3 |
| 2015/0121523 | A1* | 4/2015 | Crowley | G06Q 10/06 |
| | | | | 726/23 |
| 2015/0237106 | A1* | 8/2015 | Golay | H04L 67/02 |
| | | | | 709/203 |
| 2015/0261918 | A1* | 9/2015 | Thornbury, Jr. | G16H 10/60 |
| | | | | 705/3 |
| 2015/0358591 | A1* | 12/2015 | Kim | G08B 25/016 |
| | | | | 348/143 |
| 2016/0012182 | A1* | 1/2016 | Golay | G16H 40/20 |
| | | | | 705/3 |
| 2016/0242705 | A1* | 8/2016 | Richardson | A61B 6/035 |
| 2016/0350923 | A1* | 12/2016 | Muraoka | G06T 5/008 |
| 2017/0093832 | A1* | 3/2017 | Schwartz | G16H 10/60 |
| 2017/0231843 | A1* | 8/2017 | Thompson | A61B 6/032 |
| | | | | 378/20 |
| 2017/0300654 | A1* | 10/2017 | Stein | H04B 7/18528 |
| 2018/0092595 | A1* | 4/2018 | Chen | A61B 5/1128 |
| 2019/0114776 | A1* | 4/2019 | Balch | G06T 7/11 |
| 2019/0200274 | A1 | 6/2019 | Lautenschlaeger | |
| 2021/0295967 | A1* | 9/2021 | Nakanishi | G16H 10/65 |

* cited by examiner

METHOD FOR PROVIDING AT LEAST ONE IMAGE DATASET, STORAGE MEDIUM, COMPUTER PROGRAM PRODUCT, DATA SERVER, IMAGING DE-VICE AND TELEMEDICINE SYSTEM

PRIORITY STATEMENT

The present application hereby claims priority under 35 U.S.C. § 119 to European patent application number EP19199917.6 filed Sep. 26, 2019, the entire contents of which are hereby incorporated herein by reference.

FIELD

Embodiments of the invention generally relate to a method for providing at least one image dataset and/or a storage medium, device, stem etc.

BACKGROUND

Stroke is the third most frequent cause of death, and the leading cause of disabilities worldwide. It is a medical condition in which a disordered blood flow in the brain results in cell death. This can result in short-term and long-term complications, e.g. disabling of speech.

To avoid or minimize complications, it is necessary to minimize the time between the occurrence of the stroke and the start of a treatment. The longer it takes to start a treatment, the worse the medical outcome may be.

To treat ischemic stroke, a thrombolysis, also called fibrinolytic therapy, can be performed. Unfortunately, a thrombolysis worsens the situation in case of a hemorrhagic stroke. Hence, it is necessary to identify the illness with absolute certainty as an ischemic stroke before starting a thrombolysis. This can be done by medical imaging techniques, such as computed tomography (CT) or Magnetic Resonance Imaging (MRI).

It is known to use a so-called mobile stroke unit. A mobile stroke unit is an ambulance having an imaging device, e.g. a computed tomography scanner. Then images for diagnosis can be taken at the place where a patient is. It is equipped to examine the illness locally to save time.

EP 3 506 277 A1 discloses a mobile stroke unit. There the ambulance includes a computed tomography scanner. To examine the potential stroke, several CT-scans may get acquired and transmitted back to a hospital. However, in areas where cellular bandwidth and thus the speed of the data transfer is limited, the transmission may take a long time or even be totally interrupted.

A low speed can be caused by a slow transfer speed of the available cellular network. In this case the opinion of a remote expert cannot be used. To overcome this problem, it is suggested to determine a bandwidth information of at least one radio network and to choose a location having the best bandwidth. This avoids staying in an area having a poor bandwidth. Then the acquired CT-scans can be transmitted to the hospital fast.

SUMMARY

The inventors have discovered, however, that even if this approach is realized, there may be a considerable delay until the remote expert can pass his opinion.

At least one embodiment of the invention provides a method for providing at least one image dataset for remote access having an improved performance.

At least one embodiment of the invention is directed to a method for providing at least one image dataset, comprising:
a) processing at least one raw image dataset acquired from a patient by an imaging device of a mobile unit to a processed image dataset,
b) generating a reduced image dataset by reducing the amount of data of the processed image dataset, and
c) storing the at least one raw image dataset and/or the processed image dataset and/or reduced image dataset on a data server, the data server being part of the mobile unit and connected to a network.

In accordance with another embodiment of the invention, a non-transitory computer-readable data storage medium encoded with programming instructions is disclosed, the storage medium being loaded into a main memory of a data server, the programming instructions causing the data server to carry out the method of at least one embodiment. Such a non-transitory computer-readable data storage medium is simply called memory in at least one embodiment of the current invention.

In accordance with another embodiment of the invention a computer program product for controlling a data server of a mobile imaging device, wherein the computer program product, when executed, is configured to cause the data server to carry out the method of at least one embodiment.

In accordance with another embodiment of the invention, a data server is disclosed, the data server having a memory and a CPU having access to the memory,
the data server being connected via a data connection to an imaging device for acquiring raw image datasets,
the CPU being adapted to processing the raw image datasets to processed image datasets and to reduce the processed image datasets to reduced image datasets,
the memory being capable of storing processed image datasets,
the data server being connected to a network,
wherein the data server is configured to carry out at least one embodiment of the method.

In accordance with another embodiment of the invention, an imaging device is disclosed comprising:
an acquisition unit for acquiring raw image datasets,
a data server, the data server being assigned to the acquisition unit and connected to a network,
the data server having a memory and a CPU having access to the memory,
the memory being capable of storing the raw image datasets,
the memory being encoded with programming instructions, the programming instructions being loaded into a main memory of the data server, the programming instructions causing the data server to carry out the method of at least one embodiment.

In accordance with another embodiment of the invention, a telemedicine system is disclosed comprising:
an imaging device for acquiring raw image datasets,
a data server, the data server being assigned to the imaging device and connected to a network,
the data server having a memory and a CPU having access to the memory,
the memory being capable of storing image datasets, and
a telemedicine device, the telemedicine device being located in or at the imaging device.

In accordance with another embodiment of the invention, a mobile unit is disclosed comprising:
an imaging device for acquiring raw image datasets,
a data server, the data server being assigned to the acquisition unit and connected to a network, the data server having a memory and a CPU having access to the memory, the memory being capable of storing the raw image datasets, the memory being encoded with programming instructions, the programming instructions being loaded into a main memory of the data server, the programming instructions causing the data server to carry out the method of at least one embodiment.

At least one embodiment is directed to a method for providing at least one image dataset, the method comprising:

processing at least one raw image dataset, acquired from a patient by an imaging device of a mobile unit, to create a processed image dataset;

generating a reduced image dataset by reducing an amount of data of the processed image dataset; and storing at least one of the at least one raw image dataset, the processed image dataset and the reduced image dataset on a data server, the data server being part of the mobile unit and being connected to a network.

At least one embodiment is directed to a non-transitory computer-readable data storage medium storing programming instructions, the storage medium being loaded into a main memory of a data server, the programming instructions causing the data server to carry out the method of an embodiment when executed by the data server.

At least one embodiment is directed to a non-transitory computer program product for controlling a data server of a mobile imaging device, storing computer instructions which, when executed, are configured to cause the data server to carry out the method of an embodiment.

At least one embodiment is directed to a data server, the data server comprising:

a memory; and a central processing unit (CPU) having access to the memory, the data server being connected via a data connection to an imaging device for acquiring raw image datasets, and being connected to a network, the CPU being adapted to process the raw image datasets acquired, to create processed image datasets, and the memory being configured to store image datasets, wherein the CPU, in conjunction with the memory of the data server, is configured to carry out at least processing at least one raw image dataset, acquired from a patient by an imaging device of a mobile unit, to create a processed image dataset, generating a reduced image dataset by reducing an amount of data of the processed image dataset, and storing at least one of the at least one raw image dataset, the processed image dataset and the reduced image dataset on a data server, the data server being part of the mobile unit and being connected to a network.

At least one embodiment is directed to an imaging device for a mobile unit, for acquiring raw image datasets, comprising:

a data server, the data server being assigned to the imaging device and being connected to a network, and the data server including a memory and a central processing unit (CPU) having access to the memory, the memory being configured to store the raw image datasets and being encoded with programming instructions, the programming instructions being loadable into a main memory of the data server, wherein the programming instructions, when executed, are configured to enable the data server to carry out is configured to carry out at least processing at least one raw image dataset, acquired from a patient by an imaging device of a mobile unit, to create a processed image dataset, generating a reduced image dataset by reducing an amount of data of the processed image dataset, and storing at least one of the at least one raw image dataset, the processed image dataset and the reduced image dataset on a data server, the data server being part of the mobile unit and being connected to a network.

At least one embodiment is directed to a telemedicine system, comprising:

the imaging device of an embodiment; and a telemedicine device, the telemedicine device being located in the mobile unit.

BRIEF DESCRIPTION OF THE DRAWINGS

Further details of the invention are provided below.

Parts that correspond to one another are labeled with the same reference characters in all figures.

DETAILED DESCRIPTION OF THE EXAMPLE EMBODIMENTS

Figure 1:
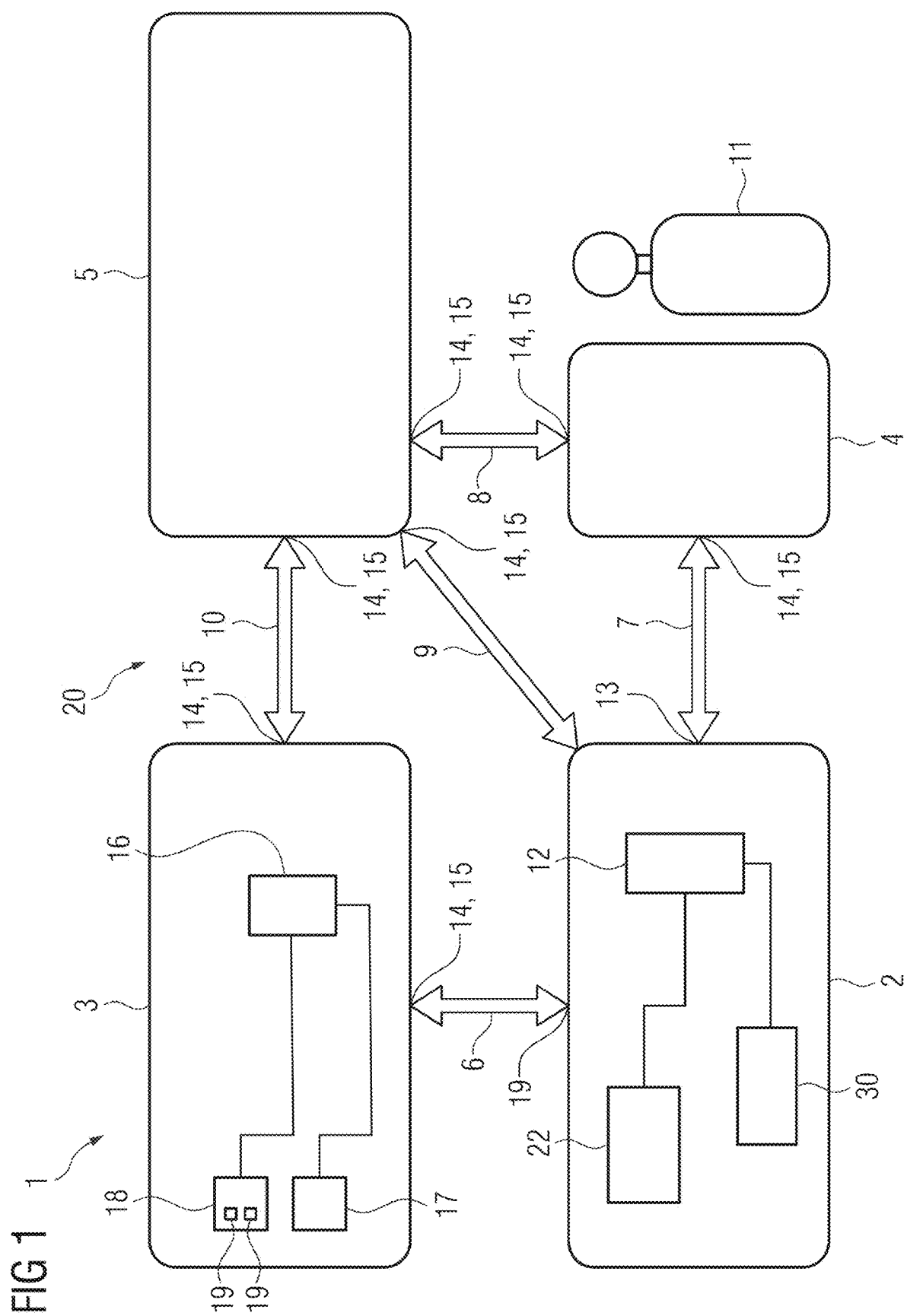
FIG. 1 shows an embodiment of a telemedicine system.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Bluray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention is directed to a method for providing at least one image dataset, comprising:
- d) processing at least one raw image dataset acquired from a patient by an imaging device of a mobile unit to a processed image dataset,
- e) generating a reduced image dataset by reducing the amount of data of the processed image dataset, and
- f) storing the at least one raw image dataset and/or the processed image dataset and/or reduced image dataset on a data server, the data server being part of the mobile unit and connected to a network.

An idea behind at least one embodiment of the invention is to provide an automatic reconstruction of the acquired image datasets such that the amount of data is reduced to the necessary minimum without compromising on quality. Therefore the processed image datasets are reduced.

Preferably, the number of slices is reduced. In particular, the number of slices of the reduced image dataset or datasets may be smaller than the number of lines of the detector used for acquiring the raw image dataset or raw image datasets. In case of CT a CT scanner including a multi-line detector may be used. A multi-line detector has for example one hundred lines. Usually one to several thousand raw images are acquired. They are reconstructed to a three dimensional processed dataset having one hundred slices. By reducing the number of slices of the processed image dataset the amount of data to be transferred can be minimized.

Preferably, a given number of slices is merged to one slice. For example, five slices are merged to one slice, respectively. Then one hundred slices can be reduced to twenty slices.

Advantageously, a number of at least five lines is merged to one slice. Moreover, a number of at least ten lines is merged to one slice.

The lines can be merged by averaging respective picture elements. Respective picture elements are picture elements that have the same indices but differ in the slice they belong to. This method is a kind of multiplanar reconstruction (MPR), namely an average intensity projection (AIP).

Alternatively, the number of slices can be reduced by, at each pixel, using the maximum value of the slices to be reduced. This is called maximum intensity projection (MIP).

Preferably a remote expert gets access to the data server via the network. This may be carried out while the patient still lies on a patient table of the imaging device and further images are being acquired. Hence the remote expert has access to the image datasets as soon as possible.

The expert may have access during or after the completion of the reduction of the image datasets. Then the data server of the mobile unit works as a kind of streaming server. This similar to video streaming services which allow to start watching a movie, although the TV apparatus just downloaded the first 10 seconds.

An image dataset can be a raw image dataset or a processed image dataset. MR raw datasets at least have to be Fourier-transformed to become a processed image dataset, CT-scans are Radon-transformed, etc. The difference between a raw image dataset and a processed image dataset hence are the steps of processing. If there is no need for processing the image dataset, the raw image dataset is identical to the processed image dataset.

Preferably, the imaging device is a medical imaging device. Advantageously, the imaging device may be a CT scanner. Alternatively, the imaging device may be a magnetic resonance apparatus and/or an X-ray apparatus and/or an ultrasound device. Magnetic resonance is also a known possibility to acquire images helping to determine an ischemic stroke.

Moreover, the mobile unit may be configured as an ambulance. The imaging device may be arranged within the ambulance. Therefore, the imaging device is preferably a mobile imaging device. In particular, the ambulance can be equipped as mobile stroke unit (MSU). Additionally, to an imaging device there may be a laboratory allowing specific examinations with regards to stroke. This laboratory is termed a Point-of-Care (PoC)-device.

Furthermore, the method can be used for every mobile imaging device, also for mobile imaging devices being inside a hospital.

The data server is assigned at least to the mobile imaging device. It is usually close by the mobile imaging device, e.g. in the same ambulance, and is usually connected to or by a local (wired or wireless) data connection, e.g. LAN, WLAN, Bluetooth etc. If there are more electronic devices, in particular more computer devices, e.g. a telemedicine device, they also can have access to the data server.

The data server is connected to a network so that it can be accessed from outside. Therefore, the data server at least has both a memory and a CPU. It additionally provides a server software to provide access from outside. Common protocols to provide access are VPN, SSH, WebDAV, FTP, SFTP, and so on. The data server also includes hardware to connect to the network, e.g. a WLAN module or a cellular network module.

In other words, the data server is a cloud server, in particular a short-/mid-term cloud server hosting the data of the patient being examined. It grants access to the image datasets, either raw image datasets or processed image datasets, of the mobile imaging device. Its main function hence is storing raw and/or processed image datasets and giving access to it.

Advantageously, the network is the internet. The remote expert may receive access to the data server via a cellular phone network. Using an ambulance to transport the imaging device, the fastest connection to the remote expert can be established using a cellular phone network. Preferably, the ambulance driver may use a map showing the connection quality in the area around the place where the patient is picked up.

The remote expert may be informed or requested at any point of the examination. Advantageously, the remote expert receives access to the data server before the reduction of the processed image dataset is completed. Then the remote expert can give advice with regard to further imaging and/or providing the diagnosis immediately after the acquisition and/or processing of the first image dataset of the patient being examined.

Preferably the staff of the mobile imaging device already has contact to the remote expert before the acquisition of the images starts.

Therefore, before processing the raw image dataset, the method may comprise the step of acquiring at least one raw image dataset. This raw image dataset is acquired using the imaging device of the mobile unit. The raw image dataset may consist of at least one 2D-image dataset. In a first embodiment it may comprise several 2D-image datasets. In a second embodiment it may comprise a 3D-image dataset. The processed image dataset may then be a 3D-image dataset in both embodiments.

Already by giving the expert access to the data server of the mobile imaging device a plus in time is achieved. This enables the neurologist or any other remote physician to interact with the image datasets instantly, without waiting for the upload to a central server in a hospital to be finished; resulting in a huge time-saving. The expert can then regard the image datasets separately immediately after acquisition. He can already try to find a diagnosis while the acquisition of further image datasets is still running. In particular the remote expert can call further acquisitions to get the optimum information.

Advantageously, the raw image dataset is processed depending on the illness to be examined. Hence only information depending on the illness, in particular a stroke, may be included in the processed image.

Preferably, at least one raw image dataset is processed to a processed image dataset, and the processed image dataset is reduced by having a pre-determined lower resolution in at least one further imaging direction than the processed image dataset, and the remote expert may have access to the reduced image dataset. A lower resolution means that the same field of view is covered by a smaller number of pixels.

Usually the raw image datasets and the processed image datasets have two or three dimensions and at least the processed image dataset as well as the reduced image dataset three imaging directions. The raw image dataset can consist of a plurality of two-dimensional images. The reduced image dataset may have a lower resolution in exactly one imaging direction. Preferably, the reduced image dataset may have a pre-determined lower resolution in exactly two imaging directions. Alternatively, the reduced image dataset may have a pre-determined lower resolution in exactly three imaging direction. Advantageously, in particular in case of non-contrast enhanced CT images, the slice thickness can be set to 3 to 10 mm. A higher resolution is possible, but without use for the determination of an ischemic stroke.

Additionally, a smaller field of view in all imaging directions can be achieved by using a signal intensity threshold to suppress noise. Pixels only showing noise have no information with regard to the existence of an ischemic stroke and need not to be transferred neither to the remote expert nor to the central server. Then the transfer of an image is sped up because the transfer is limited to the relevant part of an image dataset.

Additionally, relevant parts of the reduced image dataset can be segmented to reduce the field of view. Also then only a part of the image dataset is transferred. If a remote expert wants to determine an ischemic stroke being existent or not, he only needs to see picture elements showing the head. All further parts of the body need not to be seen and not to be transferred.

Of course a segmentation and a signal intensity threshold can be used separately or combined to reduce the size of an image dataset. The mobile then includes processing software to process the raw image datasets in a desired way. It can be located on the mobile imaging device or on the data server or on the telemedicine device or any further computer device capable of processing and reducing images and connected to the data server or the mobile imaging device.

The reconstruction or processing and reducing, respectively, of the raw image dataset may be performed on a computer device of the imaging device or on the data server.

By giving the expert access to the reduced image dataset or reduced image datasets it is ensured that only the minim amount of data has to be transferred to the expert.

In case of at least two processed image datasets a list may be presented to the remote medical expert, the list listing the reduced image datasets and showing information with regard to imaging parameters and the amount of data to be transferred.

Advantageously, the patient is registered at first at a first computer device, the first computer device registering the patient at further computer devices being located in the mobile unit, in particular at the imaging device. One of the computer devices of the mobile unit may be a telemedicine device. Preferably, the patient is registered using the telemedicine device and the telemedicine device registers the patient at least at the imaging device.

Additionally, a further device the patient being registered on may be the PoC-device.

Preferably, the first computer device is a portable device. It may be the telemedicine device. It may have a monitor and/or a camera and/or a microphone.

Advantageously, the telemedicine device may be controllable via voice. Then a medical personal of the mobile unit can call an expert giving the order "Call Dr. XY" verbally.

Advantageously, a first computer device of the mobile unit automatically checks for electronic medical records of the patient being examined on at least one central server. After the registration of the patient, the medical background can be made available. This could be done with the telemedicine device as computer device. Then the operators of the MSU and also the remote expert can consider the medical background of the patient. The first computer device stores the electronic medical records on the data server, and gives access to the electronic medical records to the remote expert and to operators of the mobile unit. All persons taking care of the patient are provided with information regarding the health history of the patient.

This enables an automatic linkage of all patient data, more profound diagnosis, faster workflow and saves effort by abolishing manual linking steps.

As soon as the data is reconstructed, the data server has to perform two tasks:

First, it has to hold the image dataset or image datasets, in particular the reduced image dataset or reduced image datasets, enabling fast diagnosis and treatment initiation.

Second, is shall transmit the data of the patient being examined to the central server, in particular to a picture archiving and communication system, short PACS, of the hospital to which the patient will be brought for further treatment, e.g. for a thrombectomy. For that task preferably not only the optimized processed image datasets are transmitted, but all data from the patient's scan.

As data transfer speed is limited in the cellular transmission setup of the MSU, those two tasks have to be balanced.

Preferably, the data server uploads the patient data, in particular the raw image datasets and/or the processed image datasets and/or the reduced image datasets and/or the PoC-device data, to a central server in parallel to providing access of the remote expert. This server can be a PACS, of the hospital the mobile unit will drive. In hospital then the complete image data are available while the remote expert could give fast advice using only the relevant data. Here the image datasets can be in a usual form, e.g. all DICOM data of the patient are transferred.

The data server may transfer the image datasets continuously once it has started. Then it may transfer data at the same time to the remote expert and the central server.

Preferably, the access of the remote expert is given priority over the uploading to the central server. Then in a first embodiment the transfer to the central server is stopped as soon as the remote expert requires image datasets. In a second embodiment the balancing gives priority to the remote expert, who actively investigates the data on the MSU-internal data server. Only if there is remaining bandwidth available, which does not get claimed by investigating data on the MSU-internal data server, this remaining bandwidth shall be used to actively push the data to the hospital PACS.

Of course several remote experts may have access to the data server at the same time. One remote expert could be neurologist, a second one could be a chemist being excellent in interpreting the PoC-device data. Also several neurologists may have access at the same time.

Advantageously, after the patient is registered at further computer devices being located in the mobile unit, the data server uploads further electronic medical records of the patient from the further computer devices to a central server. This server again can be a picture archiving and communication system, short PACS, of the hospital the mobile unit will drive. In hospital then also further electronic medical records are available.

Preferably, the data server or the telemedicine system is capable of establishing a communication between several experts. As a matter of course a communication between the personal of the mobile unit and at least on remote expert is possible. The inclusion of additional experts may be helpful to guarantee exchange between the experts.

Furthermore, the access of a remote expert to the data server may be restricted. He may get access to the data server only via a request of the mobile unit where the access is limited to some or all patient data. A neurologist can see only the image data and a chemist only the PoC-device data, all of them of the patient currently being examined. Alternatively, every requested expert has access to all data of the patient currently being examined.

Additionally, the data server may transfer the patient data, in particular the raw image datasets and/or the processed image datasets and/or reduced image datasets and/or the PoC-device data, to a cloud server. A cloud server is here a central server of a service provider. Then the patient data are transferred from the data server of the mobile unit to the cloud server and from the cloud server to the central server, e.g. the PACS, of a hospital.

There are two advantages using a cloud server. First the cloud server usually provides services to automatically upload new data. No measure has to be taken to get the data server and the cloud server synchronized. In the same way the central server is kept up to date. Synchronization is automatically done.

Second the patient data are backed up automatically. Using the cloud server as intermediate station, a backup is done without additional efforts.

The method works as well for a single raw image dataset and/or processed image dataset and/or reduced image dataset as for several raw image datasets and/or processed image datasets and/or reduced image datasets.

In accordance with another embodiment of the invention, a non-transitory computer-readable data storage medium encoded with programming instructions is disclosed, the storage medium being loaded into a main memory of a data server, the programming instructions causing the data server to carry out the method of at least one embodiment. Such a non-transitory computer-readable data storage medium is simply called memory in at least one embodiment of the current invention.

A main memory is working faster but often transient.

Each of the embodiments described with regard to the method also can be realized in the data storage medium.

In accordance with another embodiment of the invention a computer program product for controlling a data server of a mobile imaging device, wherein the computer program product, when executed, is configured to cause the data server to carry out the method of at least one embodiment.

Each of the embodiments described with regard to the method and/or the non-transient memory also can be realized in the data storage medium.

In accordance with another embodiment of the invention, a data server is disclosed, the data server having a memory and a CPU having access to the memory,
    the data server being connected via a data connection to an imaging device for acquiring raw image datasets,
    the CPU being adapted to processing the raw image datasets to processed image datasets and to reduce the processed image datasets to reduced image datasets,
    the memory being capable of storing processed image datasets,
    the data server being connected to a network,
    wherein the data server is configured to carry out at least one embodiment of the method.

Each of the embodiments described with regard to the method and/or the non-transient data storage medium and/or the computer program product also can be realized in the data server.

In accordance with another embodiment of the invention, an imaging device is disclosed comprising:
    an acquisition unit for acquiring raw image datasets,
    a data server, the data server being assigned to the acquisition unit and connected to a network,
    the data server having a memory and a CPU having access to the memory,
    the memory being capable of storing the raw image datasets,
    the memory being encoded with programming instructions, the programming instructions being loaded into a main memory of the data server, the programming instructions causing the data server to carry out the method of at least one embodiment.

Each of the embodiments described with regard to the method and/or the non-transient data storage medium and/or the computer program product and/or the data server also can be realized in the imaging device.

Preferably, the mobile imaging device is configured as CT scanner. Alternatively, the mobile imaging device may be a magnetic resonance apparatus. Furthermore, the mobile imaging device can be a hybrid imaging modality having more than one modality to acquire images.

The data server has at least one memory and at least one CPU. The memory is a non-transitory computer-readable memory that stores at least the raw image datasets. The imaging device may store the raw image datasets directly on the data server or transfer it from a memory of its own to the data server.

The data server is the computer device that allows access to at least one remote expert. The mobile unit may have a plurality of computer devices or computers, respectively. They all may have own memories or be include the memory of the data server as memory. Then the memory physically is located on the data server even if it is treated as an own memory of the imaging device.

The data server has a network connection. The network connection may be realized via a cellular network. This network connection may be the internet network or an intranet network. Anyway a remote expert can access the data server without being forced to stay at a certain place.

Preferably, the data server is configured to carry out the method of at least one embodiment. Then it gives access to persons or experts being outside or far from the mobile unit. To give access, the data server provides server services to do so. It may have implemented protocols like VPN, SSH, WebDAV, FTP, SFTP, and so on.

Furthermore, the data server may have software to process the raw image datasets. If so, processed image datasets optimized for transfer can be generated.

The mobile unit may be configured as ambulance. Then it is adapted to transport patients having medical equipment inside.

Advantageously, the medical unit may be a mobile stroke unit and comprise a PoC-device. This is a special kind of laboratory as described above. This PoC-device may be equipped for stroke diagnosis.

In accordance with another embodiment of the invention, a telemedicine system is disclosed comprising:
  an imaging device for acquiring raw image datasets,
  a data server, the data server being assigned to the imaging device and connected to a network,
  the data server having a memory and a CPU having access to the memory,
  the memory being capable of storing image datasets, and
  a telemedicine device, the telemedicine device being located in or at the imaging device.

Each of the embodiments described with regard to the method and/or the non-transient data storage medium and/or the computer program product and/or the data server and/or the imaging device also can be realized in the telemedicine system.

Advantageously, the telemedicine system comprises a central server, the central server being connected to the network. The central server is a server of a hospital or medical facility the mobile unit will drive.

Preferably, the telemedicine system comprises a cloud server. The cloud server is an intermediate station between the data server and the central server and usually hosted by service providers. It serves synchronization and/or backup.

Advantageously, the telemedicine system includes at least one internet device of a remote medical expert. The expert can use it for accessing the data server.

In accordance with another embodiment of the invention, a mobile unit is disclosed comprising:
  an imaging device for acquiring raw image datasets,
  a data server, the data server being assigned to the acquisition unit and connected to a network,
  the data server having a memory and a CPU having access to the memory,
  the memory being capable of storing the raw image datasets,
  the memory being encoded with programming instructions, the programming instructions being loaded into a main memory of the data server, the programming instructions causing the data server to carry out the method of at least one embodiment.

Each of the embodiments described with regard to the method and/or the non-transient data storage medium and/or the computer program product and/or the data server and/or the imaging device also can be realized in the imaging device.

FIG. 1 shows a telemedicine system 1. The telemedicine system 1 has four main components: a mobile unit 2, a hospital 3, an internet device 4 of a remote medical expert 11 and (optionally) a cloud server 5. Arrows 6, 7, 8, 9 and 10 show possible data transfer connections between the main components.

The remote medical expert 11 can access a data server 12 of the mobile unit 2 using his internet device 4, e.g. a laptop, PC, client computer, tablet computer or smart phone. This is shown by arrow 7. Expert 11 may give commands 13 to the data server 12 and can get image datasets 14 or PoC-device data 15 from data server 12.

Additionally, the remote expert 11 can communicate with the cloud server 5. He can get image datasets 14 and, if he has the permission, store image datasets 14 on the cloud server 5.

Cloud server 5 is optional, because it is no necessary part of the telemedicine system 1. Cloud server 5 is used for synchronization and backup purposes and hosted by a service provider.

Data server 12 usually transfers image datasets 14 and PoC-device data 15 on cloud server 5. Of course, if necessary, also the cloud server 5 may transfer data to data server 12.

Data server 12 may additionally or alternatively communicate with a central server 16 of hospital 3. This is shown by arrow 6. Central server 16 may be a gateway to several services provided by hospital 3. For example, there may be a PACS 17 or a memory 18 with electric medical records EMR 19. One EMR 19 includes medical data of a specific person.

All data are transferred by a network 20. The network 20 connects the mobile unit 2, in particular data server 12, internet device 4 of expert 11, cloud server 5 and central server 16. Network 20 may be the internet or possibly an intranet network. It may include a cellular network for access en route. In particular data transfer connections 6, 7 are usually via a cellular network.

Figure 2:
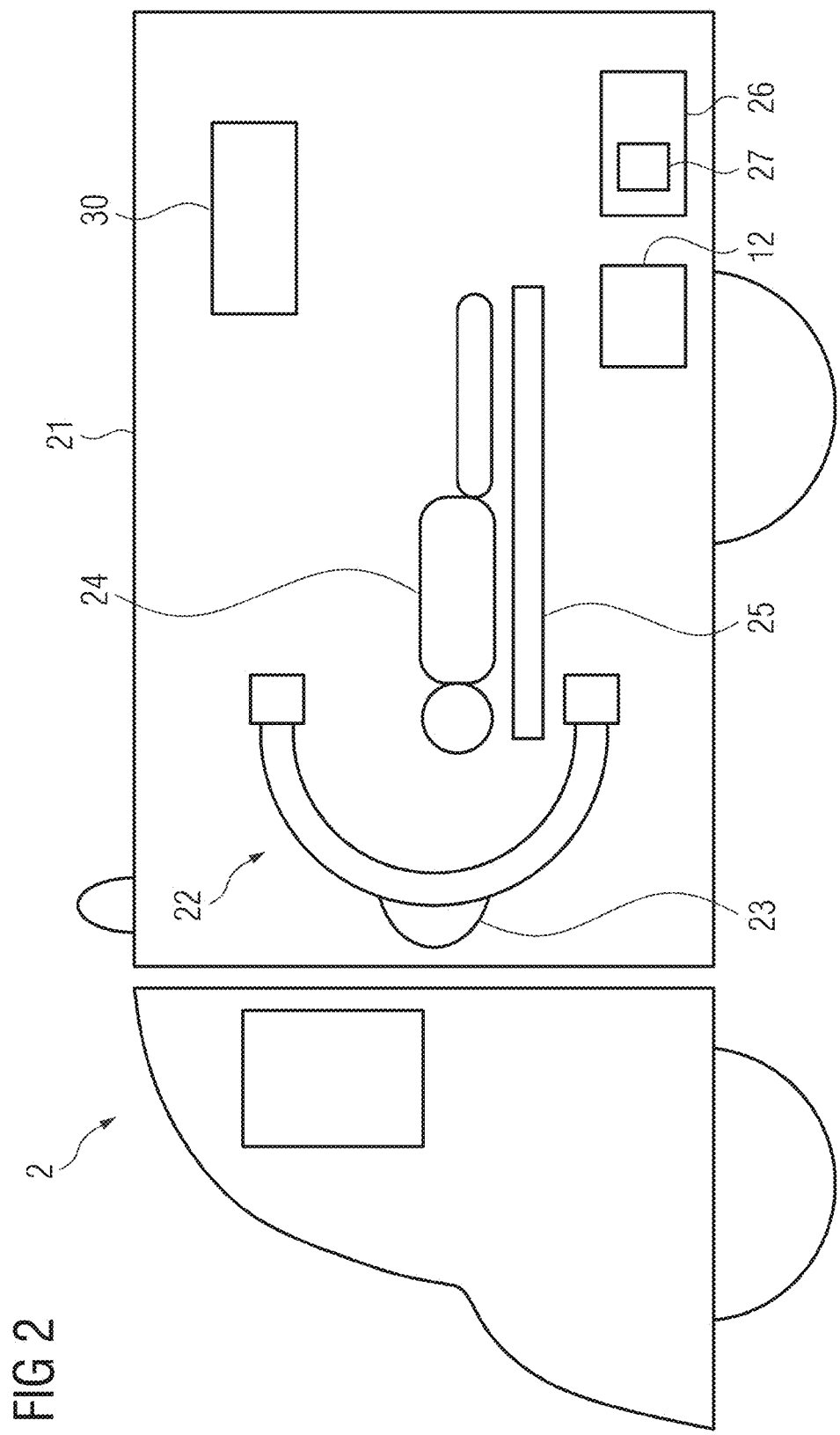
FIG. 2 shows a mobile unit in a first embodiment.

FIG. 2 shows a mobile unit 2 in a first embodiment being an ambulance 21 equipped as mobile stroke unit MSU. Therefore, it includes an imaging device 22 being a CT scanner 23.

Patient 24 may be positioned on a patient table 25. Patient table 25 may be movable to change the position of patient 24.

Additionally, ambulance 21 may comprise a PoC laboratory 26. PoC laboratory 26 preferably is equipped for stroke diagnosis and includes a computer device 27 connected to data server 12. Computer device 27 may comprise a CPU 28 and a memory 29 of its own.

Furthermore, mobile unit 2 comprises a telemedicine device 30. Telemedicine device 30 is configured to register patient 24 and to establish a communication between the personal of ambulance 21 and remote expert 11.

Figure 3:
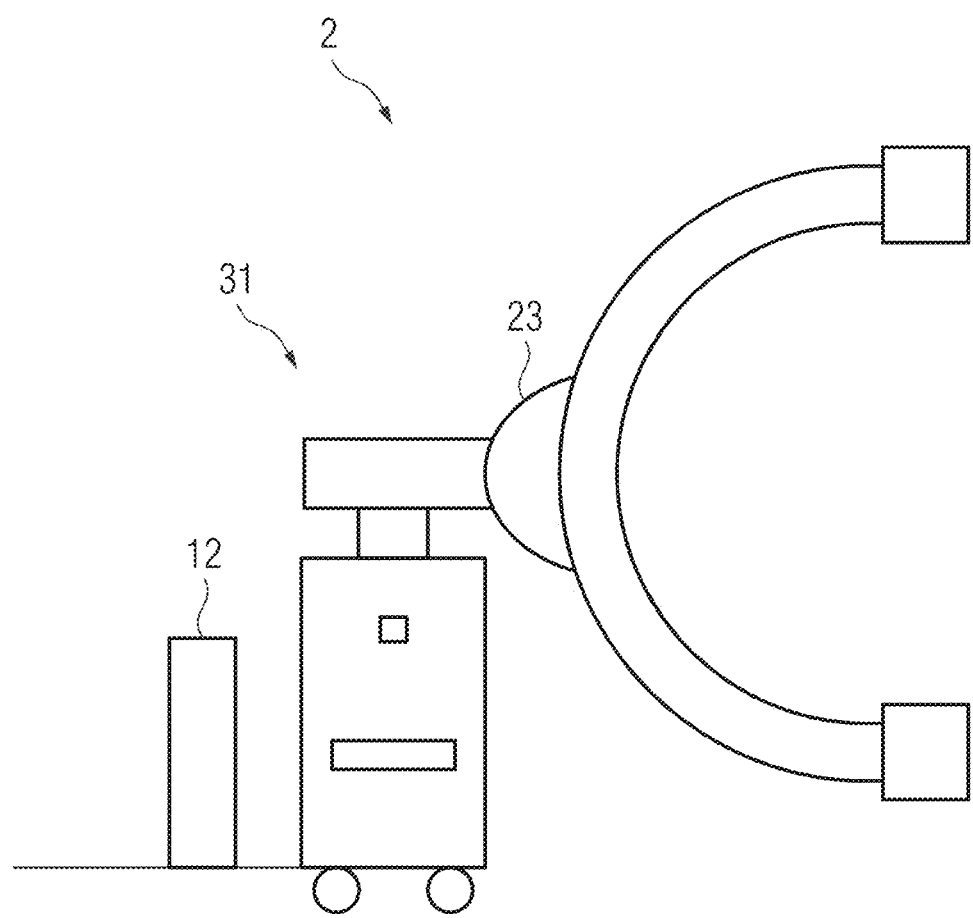
FIG. 3 shows a mobile unit in a second embodiment.

FIG. 3 shows a mobile unit 2 in a second embodiment including a movable imaging device 31 located in a hospital 5. Also there a remote expert has faster access to image datasets 14 if the proposed method is executed.

Figure 4:
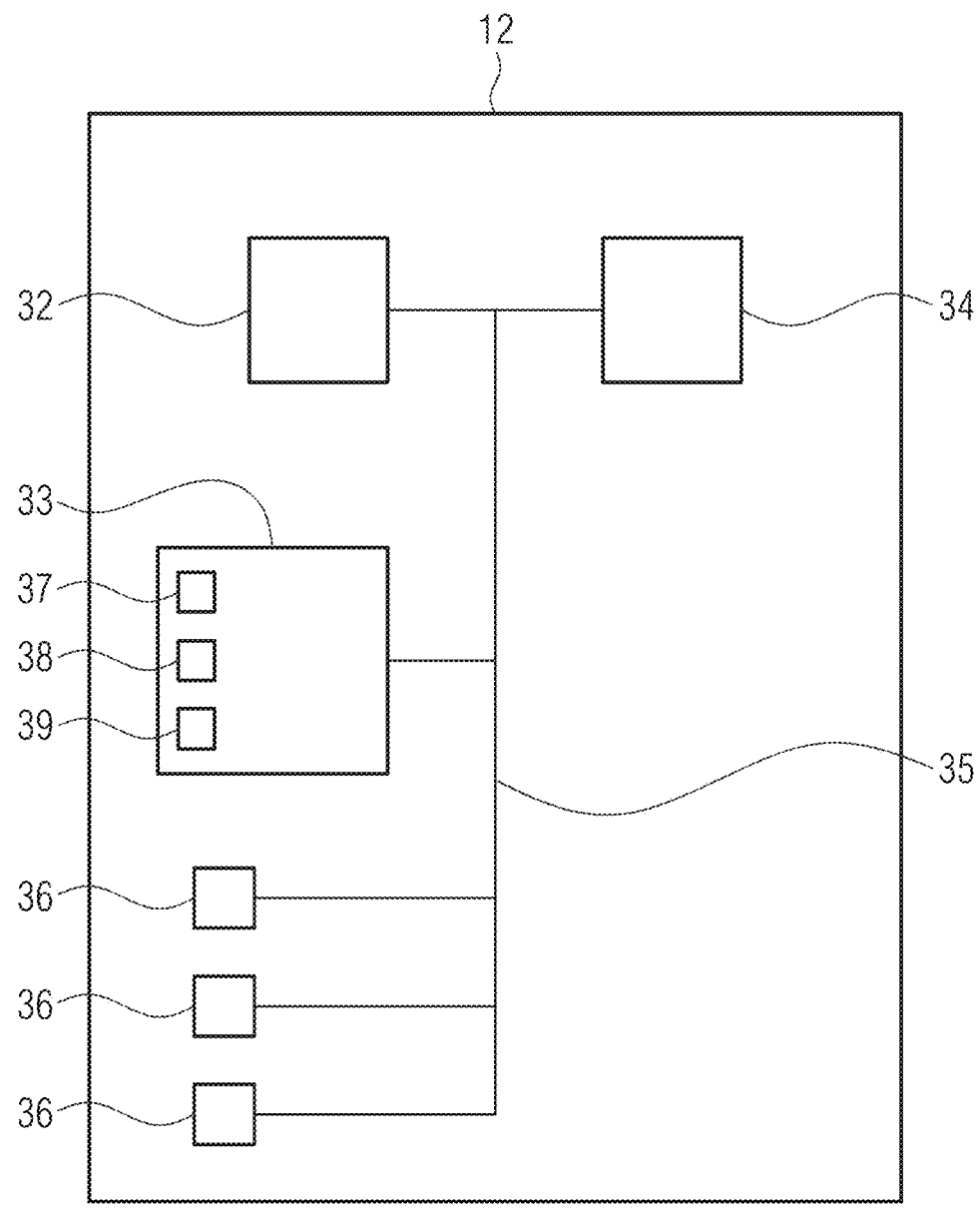
FIG. 4 shows a data server.

FIG. 4 shows an embodiment of a data server 12. Hardware components are at least a main memory 32, a non-transient memory 33, a central processing unit 34, a bus system 35 and input/output devices 36. A first one input/output device can be configured as WLAN module, a second one can be configured as cellular network connecting module, a third one can be configured as USB device.

Modern computers have the ability to follow generalized sets of operations, called programs 37 or programming instructions, respectively. Such programs 37 are stored in memory 33. If they are loaded from memory 33 into main memory 32 a user can use them. Image datasets 14 are stored in memory 33. They can be raw image datasets 38 or processed image datasets 39. To process a raw image dataset 38 it may be loaded into memory 33 and processed using one or more programs 37. Then it can be stored in non-transient memory 33 as processed image dataset 39. After that the processed image dataset can be reduced e.g. by average intensity projection, to a reduced image dataset 40.

FIG. 4 shows usual components of a computer device, in particular of a server. Data server 12 distinguishes from prior art by carrying out embodiments of the described method and by being part of a mobile unit.

Figure 5:
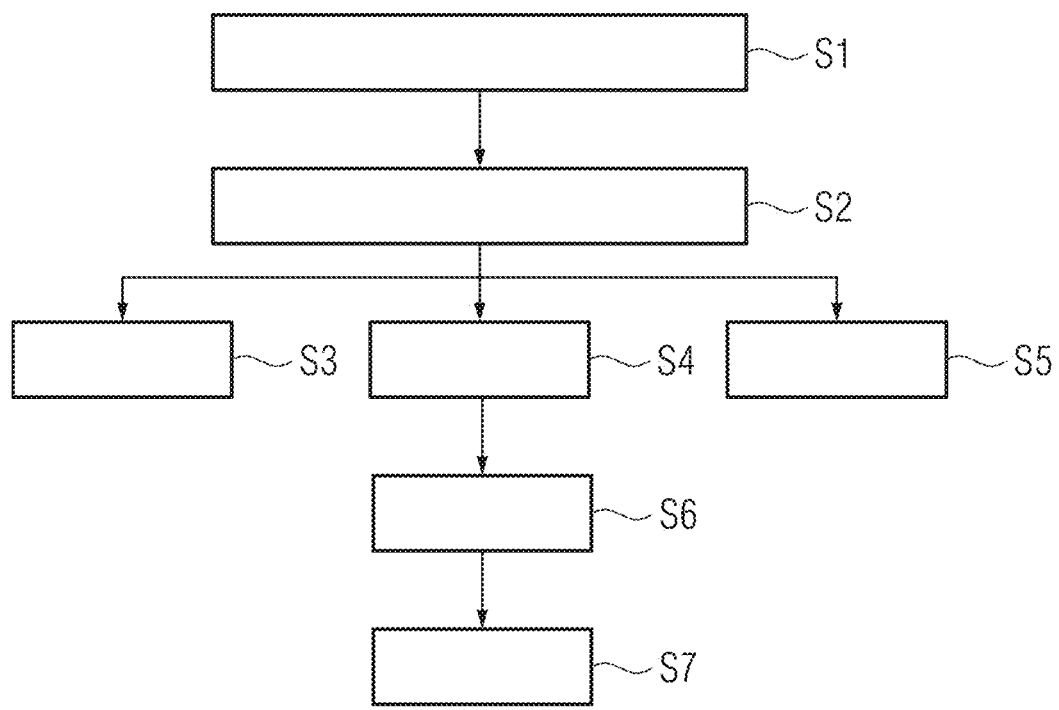
FIG. 5 shows a procedure diagram of providing image datasets to a remote expert.

FIG. 5 shows a procedure diagram of providing image datasets to a remote expert 11.

It is assumed that a patient 24 is inside ambulance 21 and it possibly has an ischemic stroke. He is not able to speak. Before performing thrombolysis this has to be clarified.

In step S1 patient 24 is registered. The registration is done using telemedicine device 30.

In step S2 telemedicine device 30 registers patient 30 at CT scanner 23 and at data server 12. It sends a DICOM Modality Worklist to the further devices.

Then CT scanner 23 loads standard imaging protocols and acquires raw image datasets 38 in step S3. This raw image dataset 38 usually is automatically processed to a processed image dataset 39 having the same number of slices as the detector of the CT scanner 23 has number of lines.

Then the processed image dataset 38 is reduced to reduced image dataset 40 by average intensity projection, where ten slices are reduced to one slice. At the same time in step S4 expert 11 is requested using telemedicine device 30. There may be a list of available experts the personal of ambulance 20 can contact. The contact may include establishing a telephone call and additionally giving access to the data of patient 24 on data server 12.

The operators of ambulance 21 communicates to a neurologist as remote medical expert 11 in step S5. Expert 11 can view at the already at least partially reduced image datasets 40. If reduced image dataset 40 is not yet completed, it can be streamed.

At the same time further raw image datasets 38 of the head of patient 24 may be acquired, processed to processed image datasets 39 and reduced to reduced image datasets 40. After having transferred or while transferring all necessary data to expert 11, telemedicine device 30 operates data server 12 to transfer all patient data, including image datasets 14 and PoC-device data 15 to cloud server 5. Thereby the transferred data are balanced by giving priority to the transfer to remote expert 11. Cloud server 5 first synchronizes its data with the data of data server 12 in step S6 and then in step S7 its data with the data stored in central server 16 or memory 18 or PACS 17, respectively.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method, by an imaging system of a mobile unit, for providing at least one image dataset, the method comprising:
   processing at least one raw image dataset, acquired from a patient by an imaging device of the mobile unit, to create a processed image dataset;
   generating a reduced image dataset by reducing an amount of data of the processed image dataset;
   storing at least one of the at least one raw image dataset, the processed image dataset or the reduced image dataset on a data server, the data server being located within the mobile unit and being connected to a network;
   uploading at least one of the at least one raw image dataset, the processed image dataset or the reduced image dataset to a central server; and
   providing a remote expert with access to the data server in parallel with the upload to the central server, the remote expert being provided access at a higher priority than the upload to the central server and the providing the remote expert with access including at least one of
   pausing the upload to the central server in response to the remote expert requesting the access, or
   balancing bandwidth allocated for the providing the remote expert with access and the upload to the central server such that the upload to the central server is allocated any remaining bandwidth not used by the providing the remote expert with access.

2. The method of claim 1, wherein the network is the internet, and the method further comprises:
   providing, to the remote expert, access to the data server via a cellular phone network.

3. The method of claim 2, wherein
the processing the at least one raw image dataset includes creating the processed image dataset to include at least one of
a relatively lower resolution than the at least one raw image dataset, or
a relatively smaller field of view in at least one image direction than the
at least one raw image dataset, and
the method further includes providing access to the processed image dataset to the remote expert.

4. The method of claim 2, further comprising:
checking, by a first computer device, for electronic medical records of the patient being examined on the central server;
storing, by the first computer device, the electronic medical records on the data server; and
providing access to the electronic medical records to the remote expert and to operators of the mobile unit.

5. The method of claim 1, wherein
the processing the at least one raw image dataset includes creating the processed image dataset to include at least one of
a relatively lower resolution than the at least one raw image dataset, or
a relatively smaller field of view in at least one image direction than the
at least one raw image dataset, and
the method further includes providing access to the processed image dataset to the remote expert.

6. The method of claim 1, further comprising:
checking, by a first computer device, for electronic medical records of the patient being examined on the central server;
storing, by the first computer device, the electronic medical records on the data server; and
providing access to the electronic medical records to the remote expert and to operators of the mobile unit.

7. The method of claim 1, further comprising
registering the patient at a first computer device; and
registering, by the first computer device, the patient at further computer devices located in the mobile unit.

8. The method of claim 7, wherein the first computer device is a portable computer device.

9. The method of claim 7, further comprising:
uploading, by the data server, further electronic medical records of the patient from the further computer devices to the central server after the patient is registered at the further computer devices.

10. The method of claim 9, further comprising:
uploading, by the data server, at least one of the at least one raw image dataset or the processed image dataset to a cloud server.

11. The method of claim 7, further comprising:
registering, by the first computer device, the patient at the imaging device.

12. A non-transitory computer-readable data storage medium storing programming instructions, the storage medium being loaded into a main memory of a server, the programming instructions configured to cause the server to carry out the method of claim 1 when executed by the server.

13. A non-transitory computer program product storing computer instructions for controlling a data server of a mobile imaging device, the computer instructions, when executed, cause the data server to carry out the method of claim 1.

14. The method of claim 1, wherein the providing the remote expert with access includes providing a plurality of remote experts with access to the data server in parallel with the upload to the central server.

15. A data server for a mobile unit, the data server comprising:
a memory; and
a central processing unit (CPU) having access to the memory,
the data server being connected via a data connection to an imaging device for acquiring raw image datasets, and being connected to a network,
the memory being configured to store image datasets, and the CPU, in conjunction with the memory, is configured to
process at least one raw image dataset, acquired from a patient by an imaging device of the mobile unit, to create a processed image dataset,
generate a reduced image dataset by reducing an amount of data of the processed image dataset,
store at least one of the at least one raw image dataset, the processed image dataset or the reduced image dataset on the data server, the data server being located within the mobile unit,
upload at least one of the at least one raw image dataset, the processed image dataset or the reduced image dataset to a central server, and
provide a remote expert with access to the data server in parallel with the upload to the central server, the access of the remote expert being given higher priority than the upload to the central server, and the providing the remote expert with access including at least one of
pausing the upload to the central server in response to the remote expert requesting the access, or
balancing bandwidth allocated for the providing the remote expert with access and the upload to the central server such that the upload to the central server is allocated any remaining bandwidth not used by the providing the remote expert with access.

16. An imaging device for a mobile unit, for acquiring raw image datasets, the imaging device comprising:
a data server, the data server being assigned to the imaging device and being connected to a network, and the data server including a memory and a central processing unit (CPU) having access to the memory,
the memory being configured to store the raw image datasets and being encoded with programming instructions, the programming instructions being loadable into a main memory of the data server,
wherein the programming instructions, when executed, cause the data server to
process at least one raw image dataset, acquired from a patient by the imaging device of the mobile unit, to create a processed image dataset,
generate a reduced image dataset by reducing an amount of data of the processed image dataset,
store at least one of the at least one raw image dataset, the processed image dataset or the reduced image dataset on the data server, the data server being located within the mobile unit,
upload at least one of the at least one raw image dataset, the processed image dataset or the reduced image dataset to a central server, and
provide a remote expert with access to the data server in parallel with the upload to the central server, the access of the remote expert being given higher priority than the upload to the central server, the remote expert being provided access by at least one of pausing the upload to the central server in response to the remote expert requesting the access, or balancing bandwidth allocated for the providing the remote expert with access and the upload to the central server such that the upload to the central server is allocated any remaining bandwidth not used by the providing the remote expert with access.

17. A telemedicine system, comprising:

the imaging device of claim 16; and a telemedicine device, the telemedicine device being located in the mobile unit.

\* \* \* \* \*